United States Patent [19]

Sabolich

[11] Patent Number: 5,246,464
[45] Date of Patent: Sep. 21, 1993

[54] ARTIFICIAL LIMB WITH ANATOMICALLY-CONFIGURED SOCKET

[75] Inventor: John A. Sabolich, Oklahoma City, Okla.

[73] Assignee: Sabolich, Inc., Oklahoma City, Okla.

[21] Appl. No.: 880,617

[22] Filed: May 8, 1992

[51] Int. Cl.⁵ .......................... A61F 2/60; A61F 2/78
[52] U.S. Cl. ........................................ 623/33; 623/37
[58] Field of Search ..................................... 623/33-38

[56] References Cited

U.S. PATENT DOCUMENTS

| | | | |
|---|---|---|---|
| 2,634,424 | 4/1953 | O'Gorman | 3/20 |
| 3,393,407 | 7/1968 | Kandel | 3/20 |
| 3,671,980 | 6/1972 | Baird | 3/20 |
| 3,889,301 | 6/1975 | Bonner, Sr. | 3/20 |
| 4,432,101 | 2/1984 | Johnson | 3/20 |
| 4,655,779 | 4/1987 | Janowiak | 623/37 |
| 4,842,608 | 6/1989 | Marx et al. | 623/33 |
| 4,872,879 | 10/1989 | Shamp | 623/36 |
| 4,911,724 | 3/1990 | Fikes | 623/37 |
| 4,921,502 | 5/1990 | Shamp | 623/33 |
| 4,923,475 | 5/1990 | Gosthnian et al. | 623/37 |
| 4,988,360 | 1/1991 | Shamp | 623/33 |
| 5,108,456 | 4/1992 | Coonan, III | 623/33 |

OTHER PUBLICATIONS

J. Sabolich. "Contoured Adducted Trochanteric-Controlled Alignment Method (CAT-CAM): Introduction and Basic Principles," Orthotics and Prosthetics, vol. 9, No. 4, pp. 15-26 (1985).

Primary Examiner—Randy C. Shay
Attorney, Agent, or Firm—Dunlap, Codding & Lee

[57] ABSTRACT

An above-the-knee prosthesis with an anatomically configured socket. The socket is characterized by one or more contours which correspond to pre-selected anatomical contours of the residual thigh. By slightly exaggerating the depth of the contour in the socket as compared with the corresponding contour in the thigh, the socket grips the residual thigh and maintains the femur in proper alignment and prevents rotation. Thus, discomfort and the gait abnormalities common in above-the-knee prostheses are reduced or eliminated. A system of inflatable compartments may be included for adjusting the size and fit of the prosthesis. Each of the inflatable compartments corresponds to one of the anatomical contours in the socket and is separately inflatable. In this way, the patient may adjust the dimensions of the socket and, more specifically, the depths of certain contours in the socket as needed to accommodate changes in the size of the residual thigh due to fluid shifts or swelling.

19 Claims, 7 Drawing Sheets

ARTIFICIAL LIMB WITH ANATOMICALLY-CONFIGURED SOCKET

FIELD OF THE INVENTION

The present invention relates generally to artificial limbs and, more particularly, to artificial limbs having sockets.

SUMMARY OF THE INVENTION

The present invention comprises a prosthesis for the residual thigh of an above-the-knee amputee. The prosthesis comprises a limb assembly and a socket in the limb assembly. The socket is characterized by one or more of the following anatomical contours: an anterior triangular depression corresponding to the femoral triangle; a medial longitudinal inverted channel shaped to receive the gracilis muscle and the adductor longus muscle; a medial inverted triangular depression shaped substantially to conform to an inverted triangular depression on the medial aspect of the thigh defined proximally by the inferior border of the ramus and the ischium, anteriorly by the gracilis muscle, and posteriorly by the adductor magnus muscle, the semitendinosus muscle and the semimembranosus muscle; a lateral longitudinal channel shaped substantially to conform to an elongate depression on the lateral thigh defined anteriorly by the vastus lateralis muscle and posteriorly by the biceps femoris muscle (lateral head); a posterior transverse channel shaped substantially to conform to the gluteal fold; a lateral rounded depression generally corresponding to the posterior trochanteric fossa; a gluteal containment compartment formed posteriorly by a gluteal shelf shaped substantially to conform to the belly of the gluteus maximus muscle, and formed medially by an ischio-ramal shelf shaped to receive the inferior border of the ramus and the ischial tuberosity, the vertical wall of the ischio-ramal shelf defining a medial rounded depression corresponding to the obturator foramen; an anterior longitudinal inverted channel shaped to receive the large prominence of the anterior thigh formed by the body of the rectus femoris muscle and the sartorius muscle; and a lateral longitudinal inverted channel shaped to receive the large elongate prominence on the lateral aspect of the thigh formed by the underlying femoral bone and iliotibial tract.

The prosthesis may include one or more inflatable compartments shaped to correspond to the anatomical contours and means for adjusting the inflation of the inflatable compartment. The inflatable compartment and the inflation adjustment means are operatively associated with the socket for adjustment of the contour of the socket to accommodate changes in the volume of the residual thigh.

The prosthesis may also include a rigid frame inside the limb assembly for supporting the socket. In those embodiments having a gluteal containment compartment, the frame may further comprise a medial flange shaped to conform and support the vertical wall of the ischio-ramal shelf. Where a frame and an inflatable compartment are utilized, the inflatable compartment preferably is supported between the frame and the socket.

BRIEF DESCRIPTION OF THE DRAWINGS

FIG. 2 is an anterior elevational view of a socket for a prosthesis of the present invention.

FIG. 6 is a plan view of the socket shown in FIG. 2.

DETAILED DESCRIPTION OF THE PREFERRED EMBODIMENTS

The present invention relates to a prosthesis for the residual thigh of an above-the-knee amputee. The prosthesis of this invention comprises a socket shaped to conform to the anatomical features of the patient's residual thigh. The uniquely fitted socket snugly contains the thigh and maintains it, throughout the gait cycle, in proper anatomical position. This fit increases the comfort of the prosthesis and minimizes gait abnormalities common with other artificial limbs.

The prosthesis of the present invention may be provided with a system of inflatable compartments, each of which conforms to a particular one of the anatomical contours. The system of adjustably inflatable compartments allows the patient to adjust the fit of the socket from time to time as the residual thigh increases and decreases in size.

Fluctuations in the size of the residual thigh present a continuing problem for amputees. Such fluctuations result from several causes, including swelling and reduction in swelling from recent surgical wounds and occasional systemic fluid shifts which affect even the well-healed residual limb. If the fluid in the limb increases, the socket is too small and creates undue friction and pressure. If the fluid in the limb decreases, the socket is too large and the gripping effect sought to be achieved by the contoured design are reduced. The pockets of trapped air between the reduced thigh and the socket may also produce noises or flatulations.

The system of inflatable compartments permit temporary adjustments to accommodate changes in the volume or size of the residual limb. Moreover, the inflatable compartments provide an improved gripping effect which stabilizes the residual limb in the socket against vertical displacement and unwanted rotation within the socket. Thus, the fit of the prosthesis can be maintained without the cost or inconvenience of modifying or replacing the socket.

Figure 1:
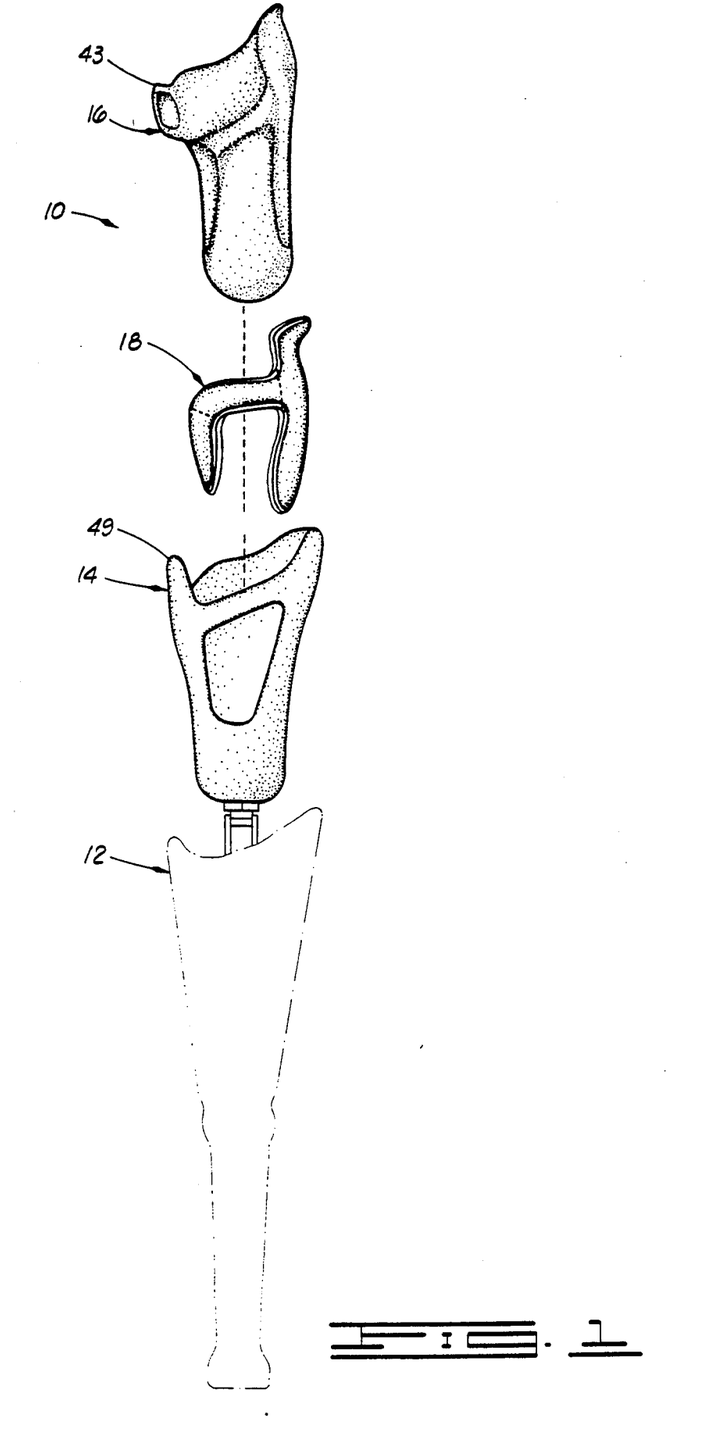
FIG. 1 is an exploded side elevational view of an prosthesis constructed in accordance with the present invention.

With reference now to the drawings in general and to FIG. 1 in particular there is shown therein an elevational, exploded view of an above-the-knee prosthesis constructed in accordance with the present invention and designated generally by the reference numeral 10. The prosthesis 10 depicted in FIG. 1 comprises generally an external lower limb 12, an internal rigid frame 14 receivable in the limb 12, a socket 16 for securing the prosthesis to the residual thigh (not shown) and a system 18 of inflatable compartments.

The present invention is directed to the unique socket design and the accompanying inflatable compartments which will be described in detail herein. The techniques for producing, selecting and assembling of the other components of the prosthesis, such as the pylon, the foot, the knee joint and a cosmetic covering, are known to those of ordinary skill in the art and will not be described in detail herein. These components will be referred to herein collectively as "the limb."

As shown in FIG. 1, the socket 16 is formed separately and adapted to be supported within the frame 14. However, in some instances the socket may be formed integrally in the upper portion of the limb. As indicated, the socket 16 is shaped to conform anatomically to the residual thigh on which it is to be worn. To this end, the socket 16 is provided with a plurality of contours which correspond to the anatomical contours of the residual limb. In most instances the socket 16 will be formed of a flexible and transparent material.

The procedure for fabricating the socket begins with a thorough interview and examination of the patient, with particular attention directed to the residual thigh. Adduction, abduction, flexion and extension are evaluated. The firmness of the tissue is observed. The presence and depth of various anatomical contours are noted and measurements are recorded. A suitable scale is utilized to note the relative depths of these contours, such as the femoral triangle, also called Scarpa's Triangle.

The depth of each anatomical depression or channel in the residual thigh is classified accordingly to scale: Class I for ¼ inch; Class II for ½ inch; Class III for ¾ inch; Class IV for 1 inch; and Class V for 1¼ inch. Similarly, the degree to which certain prominences protrude also are noted and classified as Class I, II, III, IV or V.

As used herein, the terms "depression" and "channel," when used in connection with the residual thigh, refer to areas which curve inwardly, that is, toward the inside of the thigh from the surface. Similarly, the terms "depression" and "channel," when used in connection with the socket or the model for the socket, refer to contours which curve toward the interior of the socket when viewed from the outside. Likewise, the terms "inverted channel" and "prominence" refer to contours which curve outwardly when viewed from the outside of the socket. Of course, it will be appreciated that a contour which forms a depression or channel on the outside of the socket will form a prominence or inverted channel on the inside of the socket and vice versa.

The examination of the patient proceeds by determining the midline of the body laterally by noting the position of the greater trochanter. The extent of abduction or adduction of the residual limb is noted, and whether the hips are level is observed. The ilio-femoral angle is measured.

The transverse ramus angle next is measured. This is the angle formed by the line of progression and the medial border of the ramus.

The shape of the ischial tuberosity is noted and classified as being alpha, beta or gamma.

The anterior-posterior dimension next is measured from the adductor longus muscle to the ischial tuberosity. Care is taken to compress the lateral thigh with one hand while measuring medially with a ruler. This will ensure that the measurement is not distorted as a result of tissue compression.

The length of the residual limb is measured medially from the perineum using a rigid ruler, and this is then transferred to the lateral side of the residual limb. The distance between the uppermost point of the ruler on the lateral side to the apex of the greater trochanter is taken.

Next, the skeletal medial-lateral dimension of the residual limb is measured from the ischial tuberosity to the apex of the greater trochanter. The medial-lateral dimension is taken from the ischial tuberosity parallel to the floor.

The soft tissue measurements are taken medio-laterally beginning immediately below the ischial tuberosity and ramus and then in two inch increments to the distal end of the residual limb. The angular circumference is then taken from the perineum above the trochanter. The residual limb is marked in two inch increments on the lateral side beginning at the level of the perineum. Short residual limbs should be marked in one inch increments.

It should be noted that these marks begin at the perineal level, not at the ischial tuberosity which is lower than the perineum. Failure to use this length measurement will result in a socket of insufficient length and will cause a space between the exit point of the ramus and the medial wall of the socket.

At each mark, a circumferential measurement is taken with slight tension of about ⅛ inch compression on the tissue. In the event a Silesian belt may be used, the distance between the trochanter to the anterior midline is determined. The distance from the adductor longus muscle to the greater trochanter is measured. Also the distance from the ischial tuberosity to the adductor longus muscle is measured.

Measurements are taken on the patient's unaffected limb. First, the distance between the floor and the perineum is measured. The knee center is determined, and the distance from the floor to this point is measured. To this is added about ⅞ inch for the average child and 1⅝ inch for the average adult. These distances serve as guidelines. The distance from the floor to the medial tibial plateau is measured.

The point at which the circumference of the ankle is smallest next is noted and measured. Then, the distance between this point and the floor is taken. The point at which the circumference of the calf is greatest is noted and measured. Then, the distance between this point and the floor is taken. The foot is measured and the knee width is determined.

Having completed the physical assessment of the residual thigh, a negative model of the thigh is produced by forming a cast over it. The patient is provided with well-fitting casting shorts. The shorts should be closely conformed to the body, that is, formed into the coccyx and the symphysis pubis areas. However, care should be taken that the shorts are not too tight, as this will prevent gaining access to the ischial tuberosity and the ramus during casting.

The end of the shorts which covers the residual limb is tied off and the excess material is cut away. The greater trochanter and the femoral distal relief area are marked on the shorts to allow for identification on the plaster model.

The proximal area of the residual limb is wrapped with four inch elasticated plaster bandage. The plaster then is wrapped as high as possible, ensuring that the ramus, the ischial tuberosity and ischio-rectal fossa all are contained in the plaster.

The various muscle groups are then palpated and the contours of the leg are identified and formed in the plaster. Although this phase of the fabrication procedure involves a plaster cast, reference will made to the drawings which depict a permanent flexible socket as the contours are similar.

Referring now to FIG. 2, which shows an anterior view of the socket 16, the first contour to be identified and formed in the cast preferably is the depression in the groin area known as the femoral triangle or Scarpa's Triangle. Scarpa's Triangle is defined proximally by the inguinal ligament, laterally by the sartorius muscle and medially by the adductor longus muscle. The corresponding depression in the cast (and the socket) is referred to herein as the anterior triangular depression 20.

Immediately posterior to Scarpa's Triangle is an elongate vertical prominence on medial aspect of the thigh formed by the adductor longus muscle and the gracilis muscle. A corresponding prominence, referred to herein as the medial longitudinal inverted channel 22, is formed in the cast.

Figure 3:
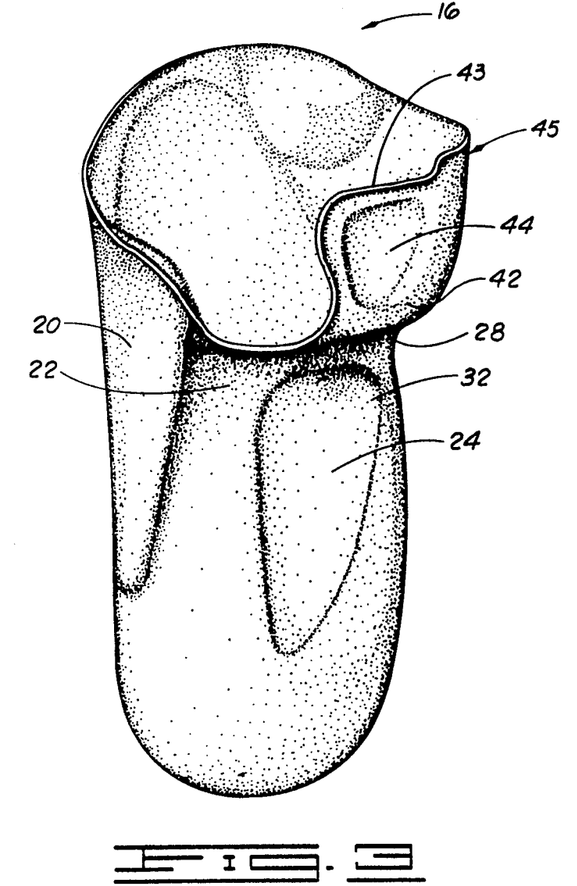
FIG. 3 is a medial elevational view of the socket shown in FIG. 2.

Continuing to move medially, and turning now to FIG. 3 which shows the medial view of the socket 16, there is an inverted triangular contour on the medial aspect of the thigh. This contour is defined proximally by the inferior border of the ramus of the ischium, anteriorly by the gracilis muscle, and posteriorly by group of underlying muscles including the adductor magnus muscle, the semitendinosus muscle and the semimembranosus muscle. A corresponding depression is formed in the cast, which depression is referred to herein as the medial inverted triangular depression 24.

Figure 4:
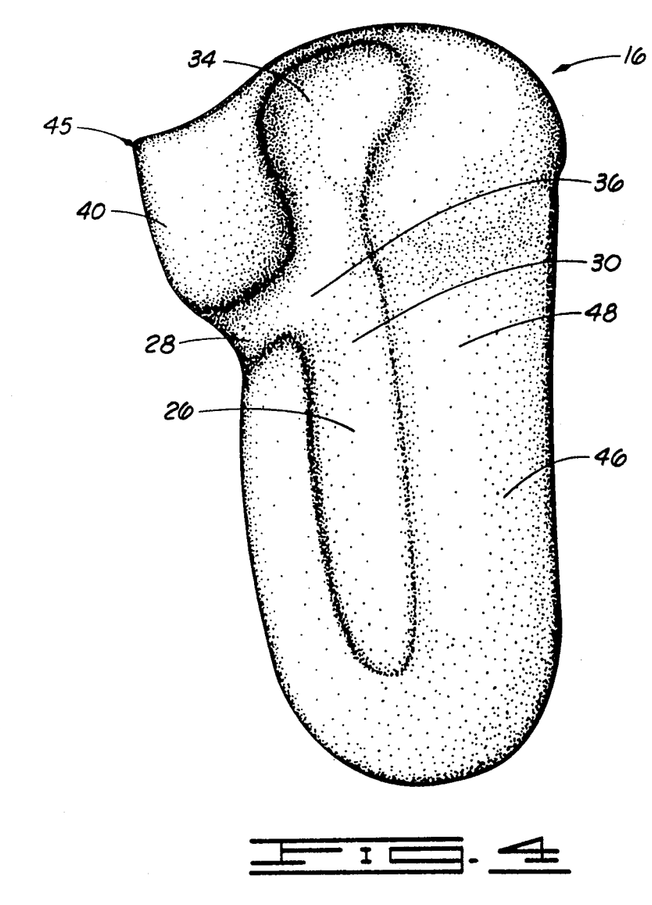
FIG. 4 is a lateral elevational view of the socket shown in FIG. 2.

Referring now to FIG. 4, on the lateral side of the thigh there is an elongate vertical channel defined by shape of the adjacent underlying muscles, such as the vastus lateralis muscle anteriorly and by the biceps femoris muscle (lateral head) posteriorly. A corresponding channel is formed in the cast, which channel is referred to herein as the lateral longitudinal channel 26.

It will be understood that the shape and dimensions of the anatomical contours described herein will vary somewhat among patients and the contours depicted in the drawings are only illustrative. Further, while in most instances all the contours identified herein will be present to some extent, one or more of the contours may be omitted depending on the needs of the patient.

In most instances the contours in the socket will be slightly exaggerted as compared to the corresponding contour on the patient's thigh. For example, in less developed or overweight patients the resting contour of the residual thigh may not distinctly exhibit one or more of the contours described herein. Yet, even in these patients, the exaggerated contouring of the socket of this invention permits the socket to "grip" the residual thigh by engaging the primary underlying muscles and bones rather than simply conforming to the outer contour of the patient's thigh at rest.

Figure 5:
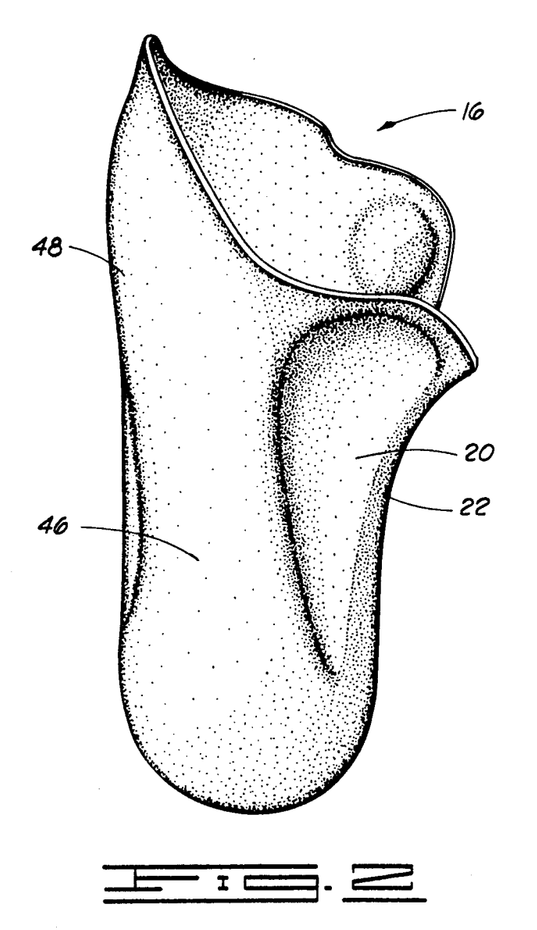
FIG. 5 is a posterior elevational view of the socket shown in FIG. 2.

Continuing now to the posterior aspect of the thigh, attention is directed to FIG. 5. An elongate transverse depression is found there which is commonly called the gluteal fold. The gluteal fold is defined proximally by the bulge or belly of the gluteus maximus muscle and distally by the area where the biceps femoris muscle (long head) and the semitendinosus muscle originate on the ischial tuberosity. A corresponding contour, referred to herein as the posterior transverse channel 28, is formed in the cast in the gluteal fold.

As shown in FIG. 5, the posterior transverse channel 28 in the socket 16 extends laterally across the back of the socket to intersect the proximal end 30 of the lateral longitudinal channel 26 (FIGS. 4 and 5) and medially to intersect the proximal medial corner 32 of the medial inverted triangular depression 24 (FIGS. 3 and 5).

Still referring to FIG. 5, proximal to the lateral longitudinal channel 26 there is formed a lateral rounded depression 34. This contour corresponds to the posterior trochanteric fossa which is seen in thin muscularly developed individuals and sometimes is referred to as "the wallet hollow." The distal or inferior aspect of the lateral rounded depression 34 is continuous with the proximal end of the lateral longitudinal channel 26 and the lateral end 36 of the posterior transverse channel 28.

With continued reference to FIG. 5, immediately proximal or superior to the posterior transverse channel 28 there is formed in the cast a gluteal shelf 40 which corresponds to the belly or bulge of the gluteus maximus muscle.

As is also seen in FIG. 5, continuous with the gluteal shelf 40 and curving around medially (see also FIG. 3), there is formed in the cast an ischio-ramal shelf 42, which is proximal to and protrudes over the medial inverted triangular depression 24. The ischio-ramal shelf 42 is shaped to contain the inferior border of the ramus and the ischial tuberosity.

Referring still to FIGS. 3 and 5 the vertical wall 43 of the ischio-ramal shelf 42 in the cast defines a medial rounded depression 44. This contour in the socket 16 corresponds to the underlying obturator foramen.

Now it can be seen that the gluteal shelf 40, the ischio-ramal shelf 42 and to some extent the lateral aspect of the socket 16 which defines the lateral rounded depression 34 together create a gluteal containment compartment 45 adapted to receive and support the ischio-rectal fossa, parts of the gluteus maximus and gluteus medius muscles and the associated bony and muscular formations of the buttock over the residual thigh.

Returning now to FIGS. 2 and 4, and considering again the anterior aspect of the residual thigh, there is a large prominence thereon formed by the body of the rectus femoris muscle and the sartorius muscle. Over this muscular prominence there is formed in the cast a relatively large anterior longitudinal inverted channel 46 (FIGS. 2 and 4).

Finally, turning once again to the lateral aspect of the patient's residual thigh, there is another large elongate prominence formed by the underlying femoral bone and iliotibial tract. Accordingly, there is formed in the cast a corresponding lateral longitudinal inverted channel 48 for containing this prominence.

Having formed the above-described contours in the plaster, the plaster is palpated to establish that the contours contain or engage the proper underlying anatomic features. The distal end of the residual limb is pushed into adduction using the prosthetist's knee, and the cast then is allowed to set.

Once the cast, which is applied only to the upper portion of the residual limb is firm or set, the remainder of the residual limb is wrapped beginning at the distal end. Applying the plaster wrap in an upward direction, edema present in the limb is pushed upward toward the body rather than being trapped in the end of the limb.

Alignment of the cast next is verified. With the patient standing as straight as possible, a plumb line is used to establish the alignment of the lateral side from the transverse axis of the hip joint. The trochanter can be posterior or anterior to the transverse axis.

By palpating through Scarpa's Triangle in the residual thigh, the anterior border of the acetabulum is located. The distance from this point posteriorly ⅞ inch is measured to determine the approximate transverse axis of the hip joint. The gravity line bisects this point. A line then is drawn from this point to the distal area of the cast in the desired amount of flexion.

The anterior alignment line next is determined. For this measurement, the cast should be adducted as far as possible, that is, the cast should be held as close to the unaffected limb as possible. The anterior alignment line should extend through the center of the cast proximally and through the distal femur.

The cast now may be removed. Immediately following removal of the cast, while the cast still is somewhat flexible, the medial-lateral dimension of the cast is measured and compared to the desired medial-lateral measurements. The width is adjusted if necessary to within the preferred range. Again, while the negative cast still is flexible, the above-described contours of the cast are accentuated.

When the cast forming the negative model is fully set, a positive plaster model may be made from the cast. The plaster model then is used to form the final socket. To form the positive model, the cast is secured in a wall fixture and filled with plaster. After the plaster has set, the cast is placed in a vice. By cutting the cast along the lateral wall, the plaster model may be removed. The plaster model then is measured, and these measurements are compared with the pre-casting measurements taken of the residual limb.

The angles of the model are noted. Viewed from the distal end of the model the planes of the anterior, posterior and medial walls form an irregular triangle. Once the angle of the medial wall (from a horizontal plane) is established, this aspect of the cast may be modified by using a flat surform file and flattening the medial wall approximately one inch below the ischio-ramal shelf 42 (FIGS. 3 and 5) down to the distal end of the model. With a round surform file, the ramus is under cut following the exact angle of the ramus. (See pre-casting measurements for ramus angle.) In a similar manner, the vertical surface of the ischio-ramal shelf 42 is flattened parallel to the medial wall. The curvature of the ischio-ramal shelf 42 is refined with a half round surform file. All angles should be rechecked to ensure they conform to the pre-casting measurements.

The line of progression and exit point for the ramus should be established. Working from the medial aspect of the positive model to the anterior area, the proximal anterior trimline of the model is squared to the line of progression. The angle of the ischio-ramal shelf 42, the medial wall, the anterior and the posterior walls should be rechecked. It should be noted that theses angles are verified by viewing the model from the distal end, and that in order to produce the correct shape the model should be checked from this position repeatedly during the modification procedure.

The curvature of the plaster model corresponding to the medial longitudinal inverted channel 22 (FIGS. 2, 3 and 5) should be rounded using a half round surform file. The outer radius of the medial wall along the medial longitudinal inverted channel 22 should measure at least two inches. The radius should be checked with a pre-fabricated template, as the tendency is to make this too sharp and too tight a radius. A radius of less than two inches causes a corrugation effect in this area. This produces a rigid, uncomfortable socket.

The anterior wall of the plaster model next is flattened while maintaining the measured depths of the contours. The anterior triangular depression 20 (FIG. 2) is marked on the model. First a transverse line is drawn across the anterior surface of the model at the level of the perineum. The medial-lateral width of the model should be divided into thirds. A first point indicating the lateral third is marked on the transverse line. A second point two inches above or proximal to the first point is made and a vertical line is drawn from the first mark on the transverse line to the second point. Returning to the transverse line, a third point about 1¼ inch lateral to the medial end of the line is marked on the line. A fourth point is marked on the cast about four inches distal to the third point, and a vertical line is drawn from the third point on the line to the fourth point. Finally, a diagonal line is drawn connecting the fourth point below the transverse line and the second point above the transverse line.

The triangular area outlined by this procedure defines the anterior triangular depression, which corresponds to Scarpa's Triangle. The deepest point of the triangular depression is at the position of the third point on the transverse line. The depth of the depression, Class I, II, III, etc., should be verified against the pre-casting measurements of the residual limb.

The angle of the medial and lateral walls should be determined. The angle of the wall is the angle formed by the plane of the flattened surface of the wall and a vertical line, with the model supported horizontally. The lateral wall generally is about five degrees less in angulation than the medial wall. (See FIG. 6.) If the angle formed by the medial and lateral walls is too great, the posterior aspect of the socket will be too narrow. This results in the residual limb being pushed anteriorly in the socket and anterior pressure, and medial-lateral pinching of the biceps femoris muscle.

Having established the angles for the medial and lateral walls, the modification of the lateral wall may be completed. First, the lateral wall is flattened with a surform file following the lateral surface of the femur. No material should be removed from the distal end of the model, as this would decrease the volume of the distal relief area in the socket.

The length of the model is measured from the medial perineum area to the distal area. This measurement then is projected to the lateral wall, and the distance from the uppermost end of this measurement to the apex of the greater trochanter is taken. The ilio-femoral angle should be verified as correct, and the overall shape of the model should be examined for proper seating.

Posterior modification of the positive plaster model now may begin. First, the posterior transverse channel 28, corresponding to the gluteal fold under the gluteal shelf 40 (FIGS. 4 and 5), is located. This should touch gently or be adjacent or tangent to the ischial tuberosity and should intersect the lateral longitudinal channel 26. The posterior transverse channel 28 is immediately under the gluteal shelf 40 and curves with the ischial tuberosity, providing more than merely a tangent force on this bony prominence. It is important to have a two inch radius to insure the patient's comfort.

The ischio-ramal shelf 42 is blended with a half round surform file. The shape of the model and measurements are checked again. The model should be marked in two inch increments beginning at the perineum and extending to the distal area. Circumferential measurements are taken at each of the two inch marks. It may be necessary to increase or decrease the size of the model to correspond to the pre-casting measurements of the residual limb. If the measurements are correct, the modification may proceed.

Next, the various contours of the model are carved. The anterior triangular depression 20 is carved, preferably with a Scarpa's knife. Similarly, the lateral longitudinal channel 26, the medial inverted triangular depression 24 and medial rounded depression 44 are carved. The contours should be shaped to have the depths— Class I, II, II, etc.—noted in the pre-casting measurements of the residual limb. Again it should be noted that no modification should be done to the distal relief area.

The model now should be finally evaluated. The shape of the model from the distal end is inspected. The angle of the anterior wall across the anterior triangular depression 20 is examined. The degree of prominence of the anterior longitudinal inverted channel 46, which contains the rectus femoris muscle, and the medial longitudinal inverted channel 22, which receives the gracilis and the adductor longus muscle, are examined to ensure these correspond to the desired depth.

The triangular shape of the model is examined. If the posterior angles are too severe, undue pressure on the anterior wall will be exerted on the limb while standing and the patient will experience problems during sitting, especially at the exit point of the ramus. Pinching of the biceps femoris while standing or walking or sitting may occur.

The line of progression of the model in relation to the medial trimline border of the socket is verified. The lateral wall of the model is examined for stabilization of the femur and to ensure adequate room in the femoral distal relief area.

The anterior triangular depression 20 is remarked on the model using the procedure described previously. The depth of this contour should be reconfirmed.

The ischio-ramal shelf 42 (FIG. 5) and the medial rounded depression 44 should be examined. The depth of this depression should be about ¼ inch. The depths of the medial triangular depression 24, the lateral rounded depression 34, the lateral longitudinal channel 26 and the posterior transverse channel 28 all are examined, and all measurements of the model again are verified.

Having finally confirmed the correct measurements and contour configurations on the model, the diagnostic test socket may be fabricated. The test socket should have a wall thickness of 3/16 inch. The ischio-ramal shelf 42 should be at least four inches higher than the perineum.

When the test socket is completed, it is fitted carefully to the patient's residual limb. First, the limb is pulled in the socket. There should be no pressure on the ischial spine. In overweight patients it sometimes happens that the ischio-ramal shelf 42 hits the coccyx and causes pressure; the shelf 42 must be lowered until there is no contact with either the coccyx or the ischial spine. This pressure area should be checked with the limb in extension and the patent bearing weight on the socket.

Pressure on the ramus should not be excessive. Pressure on the ramus can be detected by placing one's index fingers end to end outside the ischio-ramal shelf 42. With the patient lifting his weight off the socket, both index fingers are slipped inside the vertical wall 43 of the ischio-ramal shelf 42. Then, the ramus is palpated as the patient bears down again on the socket. In this position, uneven anterior and posterior pressure can be palpated. If undue pressure is present, remove the socket and reapply it. Immediate adjustments should not be attempted.

While the socket is being reapplied and evaluated, it should be turned slightly away form the direction of the pressure. Using the same finger test, the presence of the pressure should be detected. If the pressure still is present, the socket should be relieved in this area. Once a comfortable shape has been obtained, the procedure should be repeated and the socket should be reexamined for pressure on the ischial spine during weight bearing. Again, in the case of an overweight patient, coccyx pressure should be located and relieved. When the pressure on the coccyx is removed, even weight distribution on the ramus and ischial tuberosity should be reconfirmed.

A portion of the weight on the socket 16 should be borne on the ischio-ramal shelf 42, while the remaining weight is evenly distributed through the socket. The ischio-ramal shelf 42 may not be straight, but rather slightly curved to match the medial border of the ischium. There should be slight pressure carried on the soft fatty tissue over the ischial tuberosity.

That the medial rounded depression 44 is correctly positioned over the obturator foramen fossa should be verified. The exit point of the ramus should be touching the socket 16 in this area without pressure during weight bearing. If this is not the case, correction should be made: the ischio-ramal shelf 42 at the exit point of the ramus may be too high; the angle of the medial-lateral wall may be too great in the posterior area; or, the ilio-femoral angle may be too tight.

If the patient has an adductor roll, this should be contained completely within the ischio-ramal shelf 42. The anterior triangular depression 20 should closely engage the femoral triangle. The adductor longus muscle and the gracilis muscle should be contained within the medial longitudinal inverted channel 22 of the socket. Similarly, the rectus femoris muscle and sartorius muscle should be contained within the anterior longitudinal inverted channel 46.

No tissue in the proximal area should protrude over the top of the socket. If tissue is protruding, correction is indicated: the anterior proximal wall may be too low or the medial-lateral angle may need increasing. Further, for maximum comfort, there should be relief for the anterior superior iliac spine when the patient sits.

The lateral wall of the socket should conform to the lateral thigh. If gaping is present, containment of the ischial tuberosity and the ramus should be verified. If the ramus and ischial tuberosity are well contained within the gluteal containment compartment 45 and the fit is satisfactory, the proximal lateral wall is alginated.

It is particularly important to ensure that the ischial tuberosity and ramus are contained deeply within the gluteal containment compartment 45, that the ramus is well caught and not slipping out anteriorly, and that the ramus is sitting directly on the ischio-ramal shelf 42. As shown in FIG. 1, further support for the ischio-ramal shelf 42 can be provided by using a frame 14 with a medial flange 49 shaped to conform generally to the vertical wall 43 of the shelf 42.

The greater trochanter should be contained within the proper prominence. The lateral rounded depression 34 of the socket should closely engage the post-trochanteric fossa. However, it should be understood that excessive pressure in this area can produce excessive internal rotation.

The intersection formed by the posterior transverse channel 28, the lateral longitudinal channel 26 and the lateral rounded depression 34 in the socket should be seated squarely in the corresponding anatomical depressions. The lateral femoral support should be flat and adequate to prevent abduction of the femur in the socket. The lateral distal relief area should be adequate to prevent distal pressure in the socket.

The gluteus maximus muscle should be contained securely in the gluteal shelf 40. Excessive tension should be relieved by stretching the circumference of the socket. Looseness in this area should be corrected by tightening. There should be no re-flare at the proximal trimline. There should be proper tension in the muscle belly, and all muscle groups should be properly seated.

Lateral compression of the soft tissue over the femur should be detected. For this purpose, the test socket is provided with ⅜-inch holes in this area (not shown). Pressure may be detected by using the eraser end of a pencil and probing on the tissue through the holes. Excessive pressure is present if tissue bulges excessively through the holes. This may be corrected by widening the medial-lateral or circumferential dimensions of the socket, as indicated.

Once correct fit of the test socket is achieved, the socket is aligned using an alignment apparatus. The thigh should be adducted as much as possible. The transverse angle of the hip joint should be aligned with the knee and ankle. A plumb line should be used for this purpose. Having achieved static alignment, proper alignment throughout the gait cycle should be established, as well as an accurate overall fit and patient comfort.

Having completed alignment, the distal area of the socket next is alginated. As air will be trapped in the distal relief area of the socket, provision must be made for escape of this air. The pressure of the alginate should be measured. The alginate should feel similar to the soft tissue of the thenar eminence.

The test socket is removed and the algination is examined from inside the socket. Immediately upon removal, the patient's limb should be examined carefully. Any discolorations due to pressure points should be noted for correction before the permanent socket is fabricated.

The length of the test socket from the perineum to the floor should be recorded. Proper alignment lines should be clearly marked on the test socket. Now the test socket is ready for minor adjustments indicated during the above fitting procedure.

The permanent socket next is fabricated and substituted for the test socket in the prothesis. Only minor adjustments of the prosthesis should be necessary at this point.

Now it will be understood that in the permanent socket 16 of the present invention there is a complex integration of various anatomical contours, as best appreciated from the plan view of the socket shown in FIG. 6 to which attention now is directed. From this perspective it can be seen that the socket 16 generally is triangular in cross section; a first plane defined generally by outer surfaces of the anterior triangular depression 20, a second plane defined by the outer surfaces of the medial inverted triangular depression 24, and a third plane defined generally by the outer surfaces of the lateral longitudinal channel 26. These planes are indicated by the broken lines in FIG. 6.

Those skilled in the art will recognize that this triangular configuration is a departure from the conventional quadrilateral socket, or "quad" socket, so named because it is basically square in cross section. See, e.g., J. Sabolich, "Contoured Adducted Trochanteric-Controlled Alignment Method (CAT-CAM): Introduction and Basic Principles," *Orthotics and Prosthetics*, Vol. 9, No. 4, at 15–26 (1985).

Referring still to FIG. 6, the internal configuration of the socket 16, if properly fitted to engage the corresponding anatomical structures of patient's residual thigh, quite literally will grip the underlying structures to achieve a degree of fit, femoral stability and overall comfort not previously attained in above-the-knee sockets.

Unfortunately, as indicated, fluctuations in the size or volume of the residual thigh sometimes substantially alter the socket's fit, resulting in discomfort for the patient. Heretofore, a patient experiencing such volume fluctuations was obliged to endure the discomfort or have the socket professionally refitted or replaced. The latter option was costly and inconvenient, and impractical where the volume changes were not permanent.

As indicated, the present invention provides a means by which the patient himself may make minor and temporary adjustments to the socket to accommodate occasional changes in the volume of the residual thigh. To this end, the prosthesis of the present invention may be equipped with the system of inflatable compartments, which now will be described in more detail.

Generally, each compartment is shaped to correspond to one of the contours of the socket 16, previously described. Returning briefly to FIG. 1, the system 18 may include a compartment for any one or more of the contours of the socket 16. Preferably, the system 18 includes a plurality of compartments, as this provides the patient with a wider range of sizing options.

Figure 7:
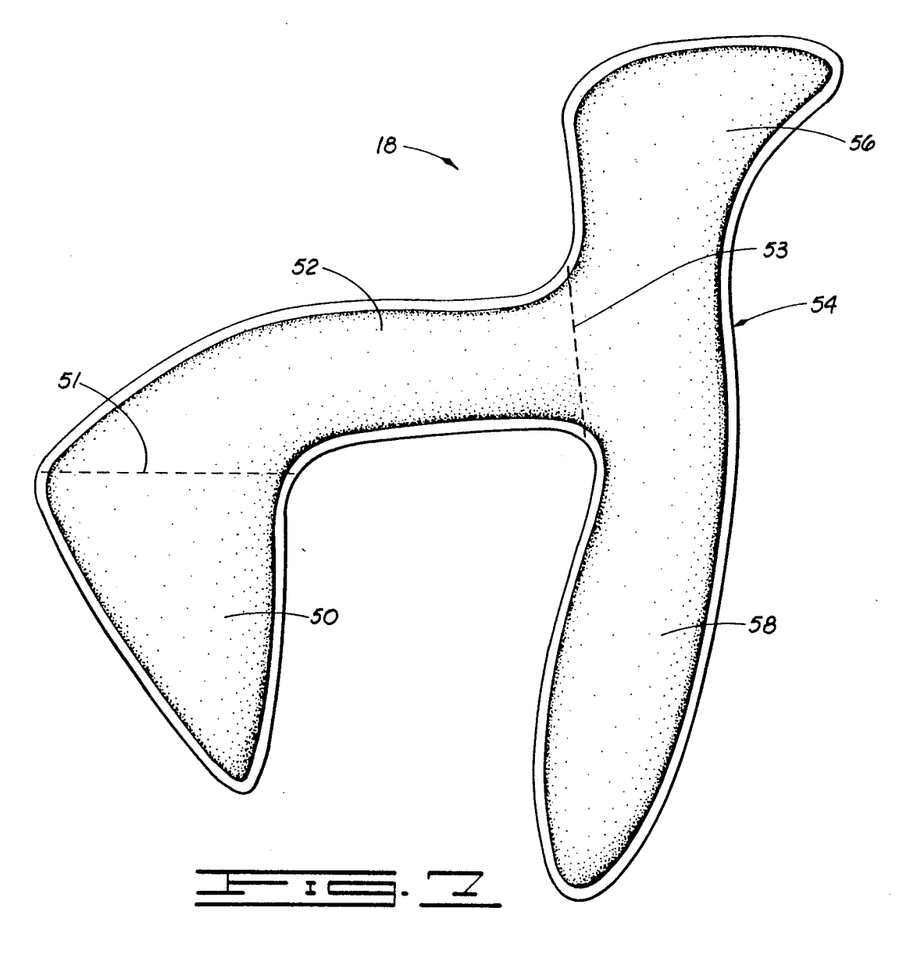
FIG. 7 is an elevational view of a system of inflatable compartments including a portion shaped to conform to the lateral longitudinal channel, the lateral rounded depression, the posterior transverse channel and the medial inverted triangular depression in the socket.

Attention now is directed to FIG. 7 showing a plan view of the system 18. With reference also to the contoured views of the socket 16 shown in FIGS. 2–5, it will be noted that the system 18 is saddle-shaped and includes three integrally formed compartments. A first compartment 50 is shaped to correspond to the medial inverted triangular depression 24; a second compartment 52 corresponds to the posterior transverse channel 28; and a third compartment 54 has an upper portion 56 which corresponds to the lateral rounded depression 34 and a lower portion 58 which corresponds to the lateral longitudinal channel 26. The three compartments 50, 52 and 54 are separated by seams 51 and 53, so that the compartments may be inflated and deflated independently.

While the system 18 of compartments shown in FIG. 7 comprises three compartments, it will be appreciated that the present invention contemplates other systems which may include different or additional compartments for the other anatomical contours. Exemplary compartments are shown in FIGS. 8-11.

Figure 8:
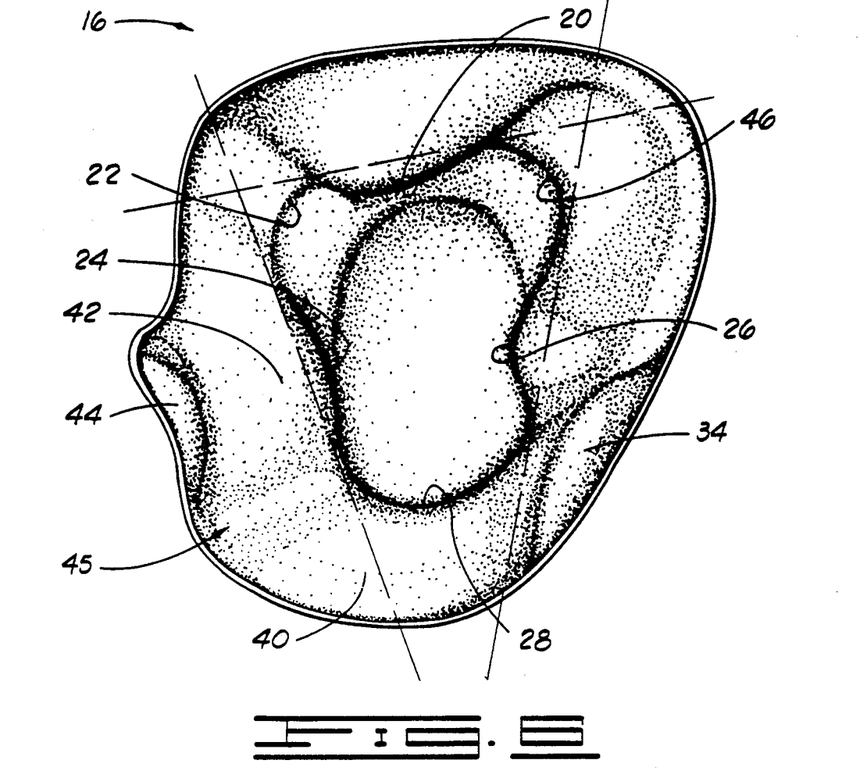
FIG. 8 is an elevational view of an inflatable compartment shaped to conform to the anterior triangular depression in the socket.

FIG. 8 shows a compartment 60 shaped to correspond to the anterior triangular depression 20.

Figure 9:
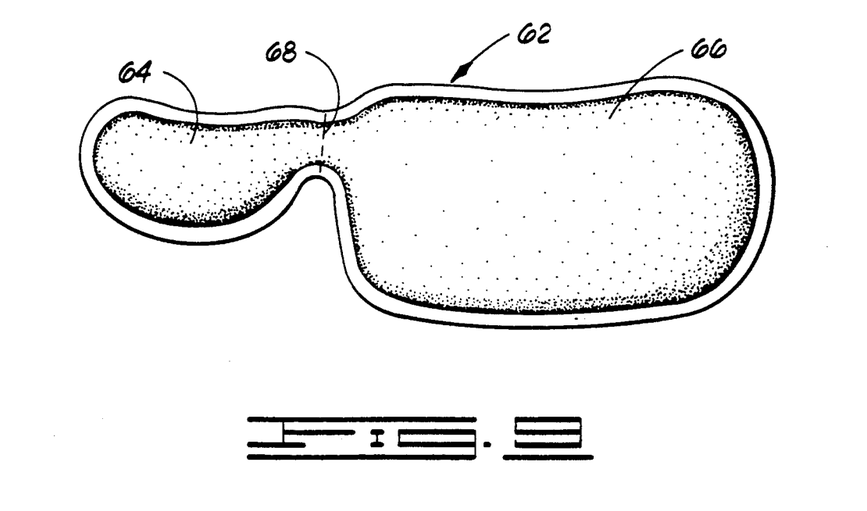
FIG. 9 is an elevational view of an inflatable compartment grouping including a portion shaped to conform to the gluteal compartment and a portion shaped to conform to the medial rounded depression in the socket.

A compartment 62, shown in FIG. 9, comprises a smaller portion 64 which corresponds to the medial rounded depression 44 over the ischio-ramal shelf 42 and larger portion 66 which corresponds to the gluteal shelf 40. The smaller and larger portions of the compartment 62 are separated by a seam 68.

Figure 10:
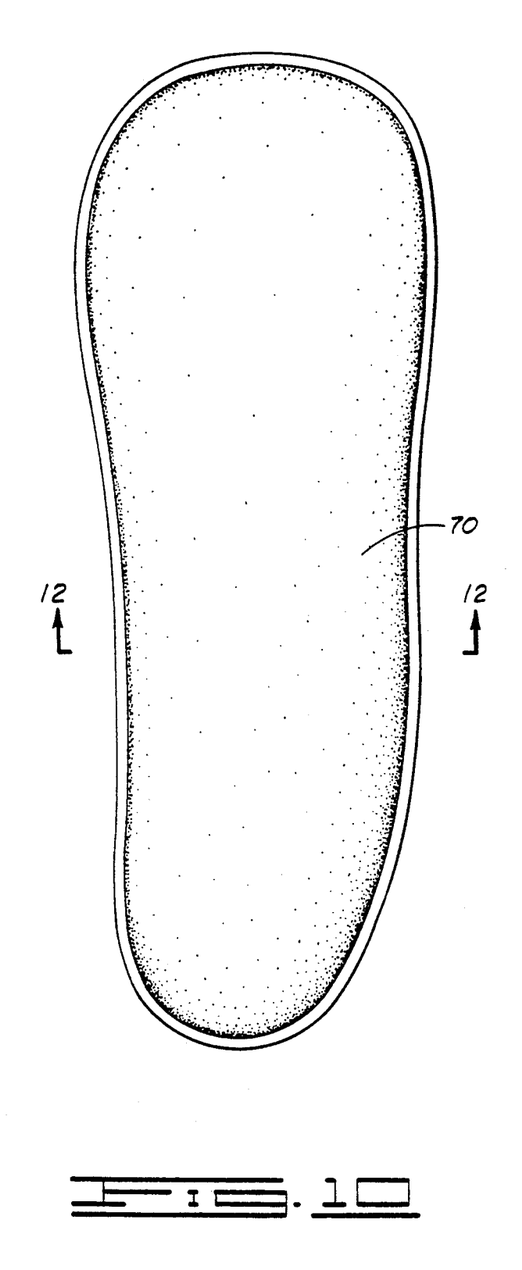
FIG. 10 is an elevational view of an inflatable compartment shaped to conform to the lateral longitudinal inverted channel in the socket.
Figure 11:
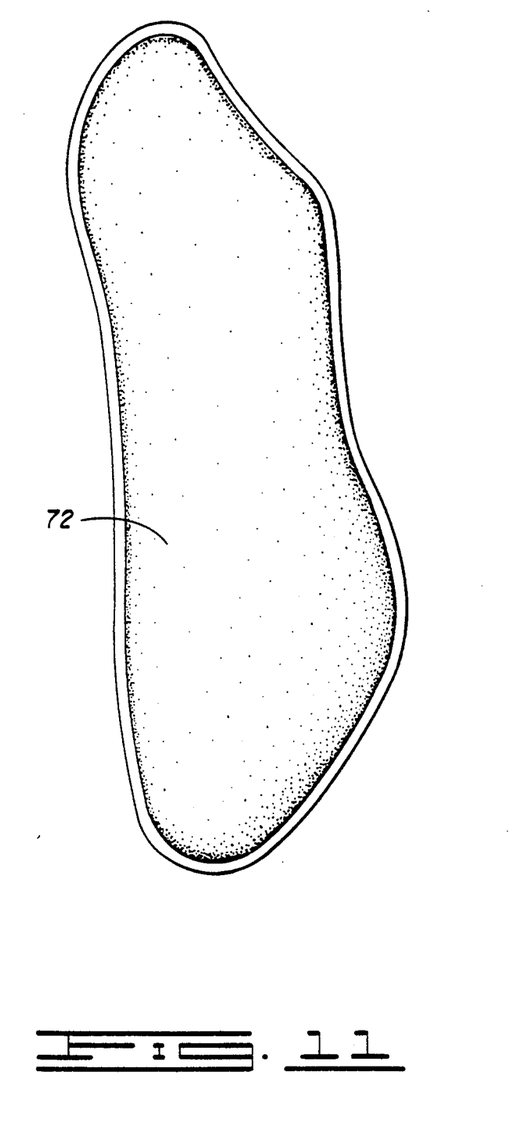
FIG. 11 is an elevational view of an inflatable compartment shaped to conform to the anterior longitudinal inverted channel in the socket.

A large elongate compartment 70, shown in FIG. 10, and an even larger elongate compartment 72, shown in FIG. 11, may be included in the system 18. These compartments correspond to the anterior longitudinal inverted channel 46 and the lateral longitudinal inverted channel 48, respectively.

Although shown separately, these compartments may be used in combination with and, if desired, attached in some manner to the system 18 (FIG. 7). Of course, the selection, shape and arrangement of these compartments will depend on the particular needs of the patient.

The system 18 of inflatable compartments is adapted for inflation with a fluid and preferably is inflated with air. To this end, the system 18 may formed of any soft, flexible material impermeable to air or the fluid used for inflation. Most preferably, the system 18 will inflated with air. In this instance the preferred material has a fabric texture and is treated so as to be heat sealable. One suitable material is 410 Denier urethan-covered nylon. The compartments, then, can be made by cutting pieces of the fabric to conform to the desired size and shape and then heat sealing the edges and seams.

Figure 12:
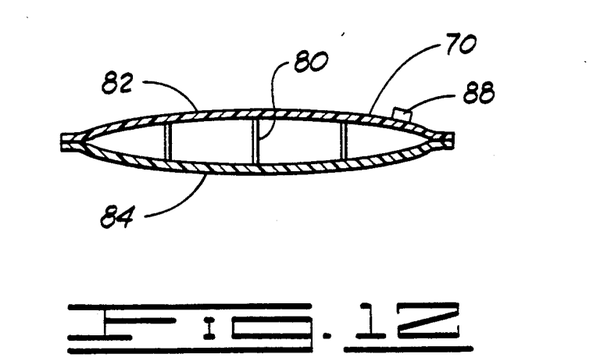
FIG. 12 is a cross-sectional view of the inflatable compartment shown in FIG. 10.

For broader compartments, interior walls or septa may be included to control the depth of the compartment as it expands. For example, a cross-sectional view of the compartment 70 (FIG. 10) is shown in FIG. 12. Septa 80 attached to the inner surfaces of the front 82 and the back 84 limit the depth to which the compartment 70 can be expanded and thus prevent the compartment from expanding into an overly rounded shape. This allows the compartments to be sized to correspond to the depth of the corresponding contours in the socket (Class I, II, III, etc.).

Figure 13:
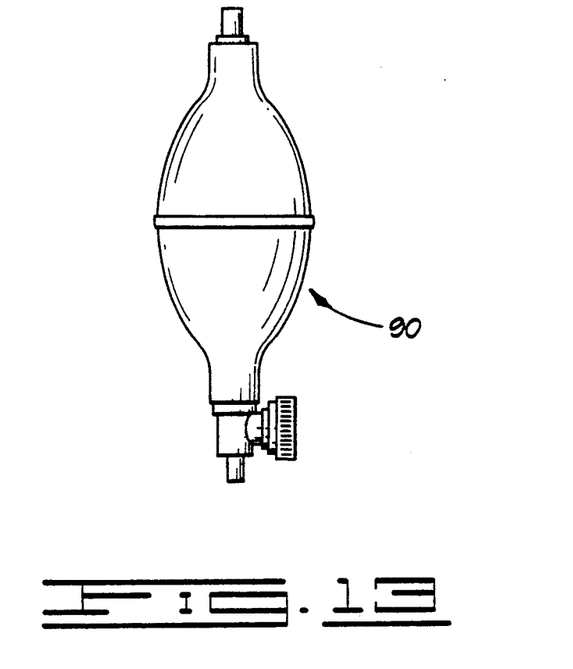
FIG. 13 is a side elevational view of a pump for inflating the inflatable compartments of the prosthesis of the present invention.

For inflating and deflating the compartments, each of the compartments may be provided with an inflation valve 88 in the wall thereof, as indicated in FIG. 12. Alternately, a valve may be attached at the end of tubing extending from the wall of the compartment. A small hand-operated air pump 90, as shown in FIG. 13, can be used to inflate the compartment. In some instances, it may be preferred to install a small pump in the wall of the compartment. The valve 88 and the pump 90 are of known construction and consequently are not shown in detail.

The system of inflatable compartments is secured to the socket in some suitable manner. For example, in the prosthesis 10 shown in FIG. 1, which includes a separately formed socket 16 and a rigid frame 14 inside the limb 12, the system 18 may be fixed between the frame and socket. Positioned thusly, inflation of any of the compartments in the system 18 will press the adjacent contour of the socket 16 inwardly, the rigid frame 14 preventing expansion of the compartment outwardly. Likewise, deflation of any of the compartments will allow the socket 16 to return to its original shape, releasing the pressure on the associated area of the residual thigh. In this way, the internal contours and the fit of the socket 16 may be adjusted to accommodate volume fluctuations in the residual thigh.

Changes may be made in the combination and arrangement of the various parts, elements, steps and procedures described herein without departing from the spirit and scope of the invention as defined in the following claims.

What is claimed is:

1. A prosthesis for the residual thigh of an above-the-knee amputee comprising:
   a limb assembly;
   a socket in the limb assembly, the socket characterized by an anterior triangular depression corresponding to the femoral triangle;
   an inflatable compartment corresponding to the anterior triangular depression;
   means for adjusting the inflation of the inflatable compartment; and
   wherein the inflatable compartment and the inflation adjustment means are operatively associated with the socket for adjustment of the contour of the socket to accommodate changes in the volume of the residual thigh.

2. A prosthesis for the residual thigh of an above-the-knee amputee comprising:
   a limb assembly; and
   a socket in the limb assembly, the socket characterized by a medial longitudinal inverted channel shaped to receive the gracilis muscle and the adductor longus muscle.

3. A prosthesis for the residual thigh of an above-the-knee amputee comprising:
   a limb assembly; and
   a socket in the limb assembly, the socket characterized by a medial inverted triangular depression shaped substantially to conform to an inverted triangular depression on the medial aspect of the thigh defined proximally by the inferior border of the ramus and the ischium, anteriorly by the gracilis muscle, and posteriorly by the adductor magnus muscle, the semitendinosus muscle and the semimembranosus muscle.

4. The prosthesis of claim 3 further comprising:
   an inflatable compartment corresponding to the medial triangular depression;
   means for adjusting the inflation of the inflatable compartment; and
   wherein the inflatable compartment and the inflation adjustment means are operatively associated with the socket for adjustment of the contour of the socket to accommodate changes in the volume of the residual thigh.

5. A prosthesis for the residual thigh of an above-the-knee amputee comprising:
   a limb assembly; and
   a socket in the limb assembly, the socket characterized by a lateral longitudinal channel shaped substantially to conform to an elongate depression on the lateral thigh defined anteriorly by the vastus lateralis muscle and posteriorly by the biceps femoris muscle (lateral head).

6. The prosthesis of claim 5 further comprising:
an inflatable compartment corresponding to the lateral longitudinal channel;
means for adjusting the inflation of the inflatable compartment; and
wherein the inflatable compartment and the inflation adjustment means are operatively associated with the socket for adjustment of the contour of the socket to accommodate changes in the volume of the residual thigh.

7. A prosthesis for the residual thigh of an above-the-knee amputee comprising:
a limb assembly; and
a socket in the limb assembly, the socket characterized by a posterior transverse channel shaped substantially to conform to the gluteal fold.

8. The prosthesis of claim 7 further comprising:
an inflatable compartment corresponding to the posterior transverse channel;
means for adjusting the inflation of the inflatable compartment; and
wherein the inflatable compartment and the inflation adjustment means are operatively associated with the socket for adjustment of the contour of the socket to accommodate changes in the volume of the residual thigh.

9. A prosthesis for the residual thigh of an above-the-knee amputee comprising:
a limb assembly; and
a socket in the limb assembly, the socket characterized by a lateral rounded depression generally corresponding to the posterior trochanteric fossa.

10. The prosthesis of claim 9 further comprising:
an inflatable compartment corresponding to the lateral rounded depression;
means for adjusting the inflation of the inflatable compartment; and
wherein the inflatable compartment and the inflation adjustment means are operatively associated with the socket for adjustment of the contour of the socket to accommodate changes in the volume of the residual thigh.

11. A prosthesis for the residual thigh of an above-the-knee amputee comprising:
a limb assembly; and
a socket in the limb assembly, the socket characterized by a gluteal containment compartment formed posteriorly by a gluteal shelf shaped substantially to conform to the belly of the gluteus maximus muscle, and formed medially by an ischio-ramal shelf shaped to receive the inferior border of the ramus and the ischial tuberosity, the vertical wall of the ischio-ramal shelf defining a medial rounded depression corresponding to the obturator foramen.

12. The prosthesis of claim 11 further comprising:
an inflatable compartment corresponding to the medial rounded depression of the ischio-ramal shelf;
means for adjusting the inflation of the inflatable compartment; and
wherein the inflatable compartment and the inflation adjustment means are operatively associated with the socket for adjustment of the contour of the socket to accommodate changes in the volume of the residual thigh.

13. The prosthesis of claim 12 further comprising:
an inflatable compartment corresponding to the gluteal shelf;
means for adjusting the inflation of the inflatable compartment; and
wherein the inflatable compartment and the inflation adjustment means are operatively associated with the socket for adjustment of the contour of the socket to accommodate changes in the volume of the residual thigh.

14. The prosthesis of claim 11 further comprising:
an inflatable compartment corresponding to the gluteal shelf;
means for adjusting the inflation of the inflatable compartment; and
wherein the inflatable compartment and the inflation adjustment means are operatively associated with the socket for adjustment of the contour of the socket to accommodate changes in the volume of the residual thigh.

15. The prosthesis of claim 11 further comprising a rigid frame positioned in the limb assembly for supporting the socket, the frame having a medial flange shaped to conform and support the vertical wall of the ischio-ramal shelf.

16. The prosthesis of claim 15 further comprising:
an inflatable compartment corresponding to the medial rounded depression in the vertical wall of the ischio-ramal shelf;
means for adjusting the inflation of the inflatable compartment; and
wherein the inflatable compartment and the inflation adjustment means are operatively associated with the socket for adjustment of the contour of the socket to accommodate changes in the volume of the residual thigh.

17. The prosthesis of claim 16 wherein the inflatable compartment is supported between the socket and the frame.

18. A prosthesis for the residual thigh of an above-the-knee amputee comprising:
a limb assembly;
a socket in the limb assembly, the socket characterized by an anterior longitudinal inverted channel shaped to receive the large prominence of the anterior thigh formed by the body of the rectus femoris muscle and the sartorius muscle;
an inflatable compartment corresponding to the anterior longitudinal inverted channel;
means for adjusting the inflation of the inflatable compartment; and
wherein the inflatable compartment and the inflation adjustment means are operatively associated with the socket for adjustment of the contour of the socket to accommodate changes in the volume of the residual thigh.

19. A prosthesis for the residual thigh of an above-the-knee amputee comprising:
a limb assembly;
a socket in the limb assembly, the socket characterized by a lateral longitudinal inverted channel shaped to receive the large elongate prominence on the lateral aspect of the thigh formed by the underlying femoral bone and iliotibial tract;
an inflatable compartment corresponding to the lateral longitudinal inverted channel;
means for adjusting the inflation of the inflatable compartment; and
wherein the inflatable compartment and inflation adjustment means are operatively associated with the socket for adjustment of the contour of the socket to accommodate changes in the volume of the residual thigh.

* * * * *

UNITED STATES PATENT AND TRADEMARK OFFICE
CERTIFICATE OF CORRECTION

PATENT NO. : 5,246,464

DATED : September 21, 1993

INVENTOR(S) : Sabolich

It is certified that error appears in the above-identified patent and that said Letters Patent is hereby corrected as shown below:

Column 1, line 39, the word "shelt" should be -- shelf --.

Column 2, line 3, the word "an" at the end of the line should be -- a --.

Column 2, line 66, the word "are" should be -- is --.

Column 5, line 21, after the word "will" please insert the word -- be --.

Column 6, line 45, after the numeral "5" please insert -- , --.

Column 8, line 5, the word "theses" should be -- these --.

Column 10, line 11, the word "patent" should be -- patient --.

Column 10, line 24, the word "form" should be -- from --.

Column 13, line 28, after the word "will" please delete -- , --.

UNITED STATES PATENT AND TRADEMARK OFFICE
CERTIFICATE OF CORRECTION

PATENT NO. : 5,246,464

DATED : September 21, 1993

INVENTOR(S) : Sabolich

It is certified that error appears in the above-identified patent and that said Letters Patent is hereby corrected as shown below:

Column 13, line 34, after the word "will" please insert the word --be--.

Signed and Sealed this

Seventeenth Day of May, 1994

BRUCE LEHMAN

*Attest:*

*Attesting Officer*     *Commissioner of Patents and Trademarks*